(12) United States Patent
Turner et al.

(10) Patent No.: US 6,180,374 B1
(45) Date of Patent: Jan. 30, 2001

(54) METHOD FOR PREPARING TERT-LEUCINE AND ANALOGUES THEREOF IN ENANTIOMERIC FORM AND INTERMEDIATES THEREIN

(75) Inventors: Nicholas Turner; James Winterman, both of Exeter; Raymond McCague, Cambridgeshire, all of (GB)

(73) Assignee: Chirotech Technology, Inc. (GB)

( * ) Notice: Under 35 U.S.C. 154(b), the term of this patent shall be extended for 0 days.

(21) Appl. No.: 09/131,466

(22) Filed: Aug. 10, 1998

Related U.S. Application Data

(63) Continuation of application No. 08/637,764, filed as application No. PCT/GB94/02392 on Nov. 1, 1994, now abandoned.

(30) Foreign Application Priority Data

Nov. 1, 1993 (GB) .................................................. 9322472

(51) Int. Cl.[7] ...................... C07C 269/00; C07C 271/02; C07C 271/22; C07C 271/50; C12P 13/06
(52) U.S. Cl. ............................... 435/116; 560/29; 560/32; 560/33; 560/39; 560/157; 560/160; 435/106
(58) Field of Search ................................. 560/29, 32, 33, 560/39, 157, 160; 435/106, 116

(56) References Cited

U.S. PATENT DOCUMENTS

| 5,219,731 | 6/1993 | Sih . |
|---|---|---|
| 5,541,080 | 7/1996 | Sih . |

OTHER PUBLICATIONS

Kiyooka, S. et al. (1993) Lewis Acid–Mediated Reaction with Silyl Ketene Acetals and Allylstannane of the Aluminum Acetals Generated by Dibalh Reduction of Alpha–Amino Acid Esters. Tetrahedron Letters 34(36): 5729–5732.
Steglich, W. et al. (1971) Umwandlung von Racem. Tert–Leucin in das L–Enantiomere. Chemische Berichte. 104(3): 687–690.
Bevinanakatti, H.S. et al. (1992) Enzymatic Synthesis of Optically Active Amino Acids. Effect of on the Enentionselectivity of Lipase–Catalysed Ring–Opening of Oxazolin–5–Ones. Tetrahedron: Assymmetry 3(12): 1505–1508.

Primary Examiner—Johann Richter
Assistant Examiner—Brian J. Davis
(74) Attorney, Agent, or Firm—Saliwanchik, Lloyd & Saliwanchik

(57) ABSTRACT

Azlactone (3), or the opposite enantiomer thereof, undergoes biotransformation, using suitable enzymatic activity, in the presence of a compound YH to form a N-acyl-amino acid (2), wherein $R^1$, $R^2$ and $R^3$ are each not hydrogen and are independently selected from groups containing up to 20 carbon atoms, optionally with any combination of $R^1$, $R^2$ and $R^3$ being joined together to form at least one ring, X is selected from groups containing up to 20 carbon atoms, and Y is selected from the group consisting of —OH, -Oalkyl and -Nalkyl. Amino acid (1), or the opposite enantiomer thereof, can be prepared in high enantiomeric excess from N-acyl amino acid (2), by converting Y to OH.

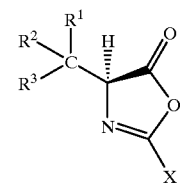

(3)

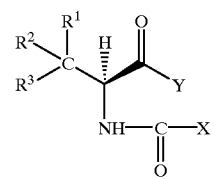

(2)

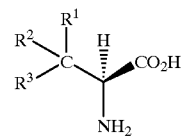

(1)

9 Claims, No Drawings

METHOD FOR PREPARING TERT-LEUCINE AND ANALOGUES THEREOF IN ENANTIOMERIC FORM AND INTERMEDIATES THEREIN

CROSS-REFERENCE TO RELATED APPLICATION

This application is a continuation of application Ser. No. 08/637,764, filed May 30, 1996 now abandoned which is a 371 of PCT/6B94/02392 filed Nov. 1, 1994.

FIELD OF THE INVENTION

This invention relates to a method for preparing tert-leucine and analogues thereof in enantiomeric form, and intermediates therein, including enantiomeric azlactones.

BACKGROUND OF THE INVENTION

Various processes for preparing tert-leucine, e.g. L-tert-leucine (Scheme 1, formula 1: $R_1=R_2=R_3=Me$) are known. See, for example, EP-A-0137372, EP-A-0248357, EP-A-0494716 and JP-A-63/211248.

Bevinakatti et al, J. Chem. Soc. Chem. Comm. (1990) 1091, and Tet. Asym. 3:1505 (1992), disclose enantioselective ring-opening of oxazolin-5-ones, and the effect of solvent on the ring-opening.

Sih et al, Tet. Lett. 33:1953 (1992), and J. Org. Chem. 58:3252 (1993), describe the enantioselective hydrolysis of oxazolin-5-ones and thiazolin-5-ones, in the context of asymmetric amino-acid synthesis.

U.S. Pat. No. 5,219,731 discloses a process for preparing optically-active amino acid derivatives comprising enantioselective enzymatic hydrolysis of oxazolone precursors, e.g. 5(4H)-oxazolone.

SUMMARY OF THE INVENTION

This invention is based on the discovery of a process for the manufacture of amino-acids of formula (1), as shown in Scheme 1 below, or their derivatives, in single enantiomer form.

According to a first aspect of the present invention, a process for preparing a N-acyl-amino-acid of formula (2), comprises biotransformation, using suitable enzymatic activity and in the presence of a base YH, of the azlactone of formula (3), wherein $R^1$, $R^2$ and $R^3$ are each a substituent that is not H and X is a substituent.

According to a second aspect of the present invention, a process for preparing an amino-acid of formula (1), or a N-acyl derivative thereof, or the opposite enantiomer, by carrying out a process according to the first aspect of the present invention, and converting Y to OH and removing X—CO—, as appropriate.

DESCRIPTION OF THE INVENTION

The amino-acids of formula (1) include three substituents $R^1$, $R^2$ and $R^3$ which are each any group except hydrogen, such as alkyl, aryl, or an oxygen or nitrogen function, e.g. tert-leucine; it will be readily understood that this definition includes any combination of $R^1$, $R^2$ and $R^3$ being joined together to form a ring or rings. This restriction, i.e. that none of $R^1$, $R^2$ and $R^3$ is H, applies since the group $R^1R^2R^3C$ must be bulky for the methodology to give a single enantiomer. In principle, it could be used to produce (1) as either enantiomer.

The process is represented by Scheme 1. The starting azlactone is made by a method known for amino-acids such as cyclisation of the N-acylated amino-acid with acetic anhydride. The azlactone is then biotransformed by means of an appropriate enzyme, typically selected from esterases, lipases and proteases. The final step involves removal of the group X—CO—.

X is chosen with regard to both biotransformation and ease of removal. Acid may remove X—CO—, as shown in Scheme 1; hydroxide ester hydrolysis may be used first. Alternatively, an enzymatic reaction may be used, e.g. with Penicillin G amidase (see EP-A-0137372); this is particularly suitable when X is aralkyl, e.g. benzyl.

Provided that they permit the reactions to run, the nature of the groups R, X and Y is not critical. Generally, each comprises no more than 10 or, possibly, 20 C atoms. For instance, X can be aryl such as phenyl or substituted phenyl, aralkyl such as benzyl, alkyl, alkoxy such as t-butoxy or benzyloxy, or aryloxy such as phenoxy. Preferably, X is benzyl or phenyl. Y can be —OH, -Oalkyl or -Nalkyl, giving respectively carboxylic acid, ester or amide, and is preferably -Oalkyl having at least two carbon atoms, and is more preferably butoxy.

For the biotransformations, suitable enzymatic activity is readily available or can be determined by simple experiment. Preferential transformation of one enantiomer of the azlactone yields one enantiomer of the amino-acid derivative. Normally a resolution process on a racemate can only yield a maximum of 50% of one isomer; however, in the process of the invention the starting azlactone undergoes racemisation such that all the material can in principle convert to one enantiomer. In order for this racemization to be efficient at relatively low concentrations of azlactone, e.g. on a non-production scale, a base (e.g. triethylamine) is preferably added to the reaction mixture in catalytic quantities.

A particular example of the invention is the case where $R^1=R^2=R^3=Me$, X=Ph and $Y=CH_3CH_2CH_2CH_2O$ which gives L-tert-leucine in more than 97% enantiomeric excess. It is noteworthy when the enzyme is LIPOZYME® (*Mucor meiheii* lipase) and the reaction is carried out in toluene solvent in the case where $R^1=R^2=Me$ and $R^3=H$ that while transformation takes place, the resulting product does not have sufficient enantiomeric excess.

The following Examples further illustrate the invention.

EXAMPLE 1 (Comparative)

2-phenyl-4-tert-butyloxazolin-5 (4H) -one (100 mg, 0.45 mmol) was shaken at 30° C., 220 rpm with LIPOZYME® (100 mg, immobilized *Mucor meiheii*), n-butanol (190 µl, 0.98 mmol) and triethylamine (15 µl, 0.2 µmol) in toluene (8 ml), for 13 days. After this time the enzyme was filtered off and the solvent removed by evaporation under reduced pressure. The resulting oil was purified by column chromatography (eluent light pretoleum: ethyl acetate [8:2]) to yield N-benzoyl tert-leucine butyl ester (85 mg, 66%).

EXAMPLE 2

N-benzoyl-DL-tert-leucine

A suspension of DL-tert-leucine (327.5 g, 2.5 mol) in water (833 ml) was cooled to 5° C. A solution of sodium hydroxide (220 g, 5.5 mol) in water (833 ml) was added dropwise over 90 min maintaining the temperature at about 5° C. After a further 30 min stirring benzoyl chloride (386 g, 2.75 mol) was added dropwise over 2.5 h keeping the temperature at about 5° C. The temperature was then allowed to warm slowly to 10° C. over 3 hours until the reaction was complete.

Ethyl acetate (2.25 l) was added and the pH adjusted to 1.5 using 6M hydrochloric acid (460 ml) keeping the temperature between 5–10° C. A white solid was precipitated which was dissolved by heating the mixture to 40° C. The two layers were separated and the organic layer concentrated to about 1 l. On cooling a white solid crystallised which was collected by filtration, washing with cold ethyl acetate, and dried (466 g, 79%). A second crop of crystals was recovered (56.0 g, 10 %).

Azlactone Formation

N-benzoyl-DL-tert-leucine (157.5 g, 0.67 mol) was suspended in 2,2,4-trimethylpentane (isooctane) (250 ml) and acetic anhydride (102 g, 1 mol) was added. The mixture was heated to reflux for 1.5 h and then switched to distillation. Isooctane was added 200 ml at a time and distilled off, removing isooctane/acetic acid azeotrope, until the still head temperature reached 99° C. The solution was then allowed to cool.

Biotransformation

The azlactone solution in isooctane (calculated to contain 138 g (0.64 mol) of azlactone in 350 ml of isooctane) was added to isooctane (340 ml) at 50° C. Butan-1-ol (87 ml, 0.95 mol) was added to the solution followed by Novo LIPOZYME® (138 g). The reaction slurry was stirred at 50° C. for 24 h. The enzyme was removed by filtration, washing with isooctane (2×200 ml). The combined organic solutions were concentrated by distillation and allowed to cool, seeding with crystals of >99% e.e. The resulting white crystals were collected by filtration to give N-benzoyl-L-tert-leucine butyl ester.

NB. Enzyme can be re-used 3 times.

N-benzoyl-L-tert-leucine butyl ester (404.5 g) was dissolved in heptane (250 ml) and hexane (250 ml) and the resulting solution allowed to cool with stirring and seeding with crystals of >99% e.e. Recovery=246.5 g, 61%, e.e. >99%.

N-benzoyl-L-tert-Leucine

N-Benzoyl-L-tert-leucine butyl ester (582 g, 200 mmol) was dissolved in methanol (200 ml). A solution of sodium hydroxide (47%, 30 ml, 500 mmol) in water (30 ml) was added over 15 minutes raising the reaction temperature to 34° C. The temperature was then kept at 35° C. for 3 hours.

The solution was concentrated to remove the methanol, and ethyl acetate (200 ml) was added. The pH was adjusted to 2 with 6M hydrochloric acid and then the two layers were separated. The aqueous layer was re-extracted with ethyl acetate (100 ml). The combined organic layers were evaporated to give a white solid. This was dissolved in hot ethyl acetate (100 ml) and after filtering the solution was allowed to cool. A white crystalline solid formed which was collected by filtration, washing with cold ethyl acetate, and dried to give N-benzoyl-L-tert-leucine (40.96 g, 87%).

L-tert-leucine

N-benzoyl-L-tert-leucine (31.5 g, 133 mmol) was suspended in water (250 ml) and potassium hydroxide (56 g, 1 mol) was added.

The mixture was then heated to reflux for 114 h at which point 91% conversion had been achieved. The solution was concentrated to 100 ml and acetone (500 ml) was added. The mixture was filtered and the solid obtained was added to hot methanol (250 ml). The undissolved solid was filtered off and the solvent evaporated to yield a white solid. This was added to water (50 ml) and the undissolved solid filtered off. Evaporation of the water gave a white solid identified by $^1$H nmr as tert-leucine, e.e. =99.4% L-tert-leucine.

EXAMPLE 3

Preparation of N-phenylacetyl-DL-tert-leucine

To a solution of DL-tert-leucine (2 g, 15.3 mol) in aqueous sodium hydroxide (2 M, 25 ml) was added dropwise phenylacetyl chloride (646 mg, 20.8 mmol), simultaneously with sodium hydroxide (2 M, 25 ml), at 0° C. over a period of 5 min. The solution was allowed to warm to room temperature and stirred for an additional 60 min until complete dissolution occurred. The reaction was then cooled to 0° C., acidified to pH 4 with conc. HCl, and stirred for 30 min. The resulting precipitate was collected by filtration, dried, and recrystallised from ethanol/water (1:1 v/v) to yield the product as a white solid (2.06 g, 54%).

Preparation of 2-benzyl-4-tert-butyloxazoline-5 (4H)-one

N-phenylacetyl-DL-tert-leucine (400 mg, 1.6 mmol) was suspended in acetic anhydride: dioxan (5 ml, 1:1 v/v) and heated for 40 min at 70° C. after which a clear solution resulted. The solution was allowed to cool to room temperature followed by removal of the solvent under reduced pressure. Traces of acetic acid were removed by re-dissolving the residue in hexane followed by evaporation affording an oil which was purified by chromatography on silica to yield the product as a clear oil (295 mg, 80%).

Biotransformation of 2-benzyl-4-tert-butyloxazolin-5(4H)-one

To a solution of 2-benzyl-4-tert-butyloxazolin-5(4H)-one in toluene was added LIPOZYME®, n-butanol and Et$_3$N. The reaction mixture was shaken in an orbital incubator at 30° C. and 220 r.p.m. for 5 days. After removal of the enzyme by filtration, the solvent was removed by evaporation under reduced pressure and the crude material purified by column chromatography (eluent light petroleum:ethyl acetate [4:1]), to N-phenylacetyl-DL-tert-leucine butyl ester (yield range 37–46%, 97% e,e).

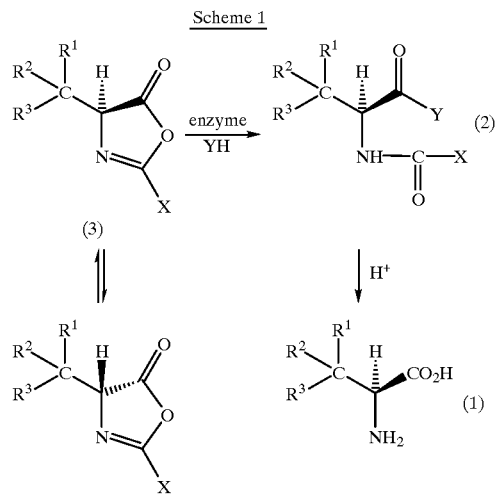

Scheme 1

What is claimed is:

1. A process for preparing a N-acyl-amino-acid derivative of formula (2)

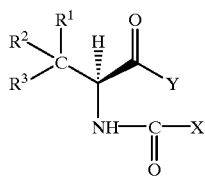

(2)

or the opposite enantiomer thereof, said method comprising biotransformation, using suitable enzymatic activity and in the presence of an alcohol YOH, of an azlactone of formula (3)

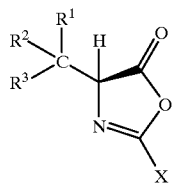

(3)

wherein $R^1$, $R^2$ and $R^3$ are each a substituent that is not H; and wherein $R^1$, $R^2$ and $R^3$ are independently alkyl or aryl and each comprises up to about 20 carbon atoms and, optionally, any combination of $R^1$, $R^2$ and $R^3$ can be joined together to form at least one ring structure; X is a substituent selected from the group consisting of aryl, aralkyl, alkyl, alkoxy or aryloxy and comprises up to about 20 carbon atoms; and Y is alkyl and comprises at least two carbon atoms.

2. The process according to claim 1, wherein X is benzyl.

3. The process according to claim 1, wherein X is phenyl.

4. The process according to claim 1, wherein $R^1=R^2=R^3=$ Me.

5. The process according to claim 1, wherein y=$CH_3CH_2CH_2CH_2O$.

6. A process for preparing an amino acid of formula (1), or a N-acyl derivative thereof,

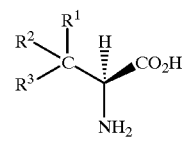

(1)

or the opposite enantiomer, comprising carrying out the process according to claim 1 and converting Y to OH and removing X—CO— from the compound shown in formula (2).

7. The process according to claim 1, wherein X is substituted phenyl.

8. The process according to claim 1, wherein X is tert-butoxy or benzyloxy.

9. The process according to claim 1, wherein X is phenoxy.

* * * * *

UNITED STATES PATENT AND TRADEMARK OFFICE
CERTIFICATE OF CORRECTION

PATENT NO. : 6,180,374 B1
DATED : January 30, 2001
INVENTOR(S) : Nicholas Turner, James Winterman, Raymond McCague Page 1 of 3

It is certified that error appears in the above-identified patent and that said Letters Patent is hereby corrected as shown below:

Column 1,
Line 9, "May 30, 1996" should read -- April 30, 1996 --.
Line 10, "PCT/6B94/02392" should read -- PCT/GB94/02392 --.

Column 2,
Line 36, "Y=CH$_3$CH$_2$CH$_2$CH$_2$O" should read -- Y=CH$_3$CH$_2$CH$_2$CH$_2$O- --.

Column 4,
Lines 45-64,

"
Scheme 1

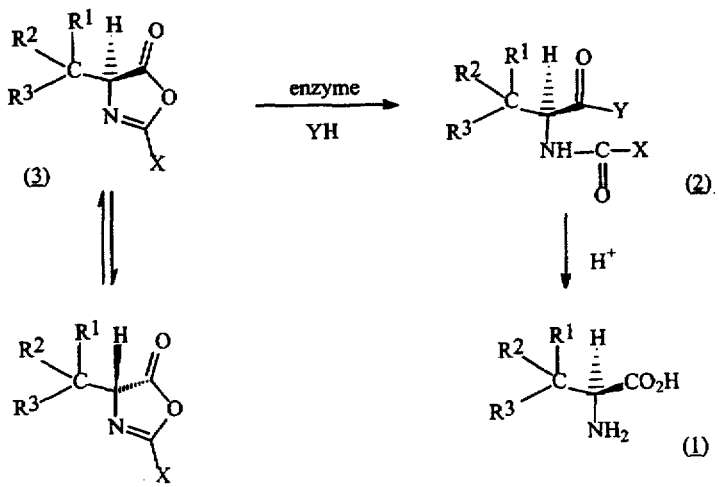
"

UNITED STATES PATENT AND TRADEMARK OFFICE
CERTIFICATE OF CORRECTION

PATENT NO.    : 6,180,374 B1
DATED         : January 30, 2001
INVENTOR(S)   : Nicholas Turner, James Winterman, Raymond McCague It is certified that error appears in the above-identified patent and that said Letters Patent is hereby corrected as shown below:

should read:

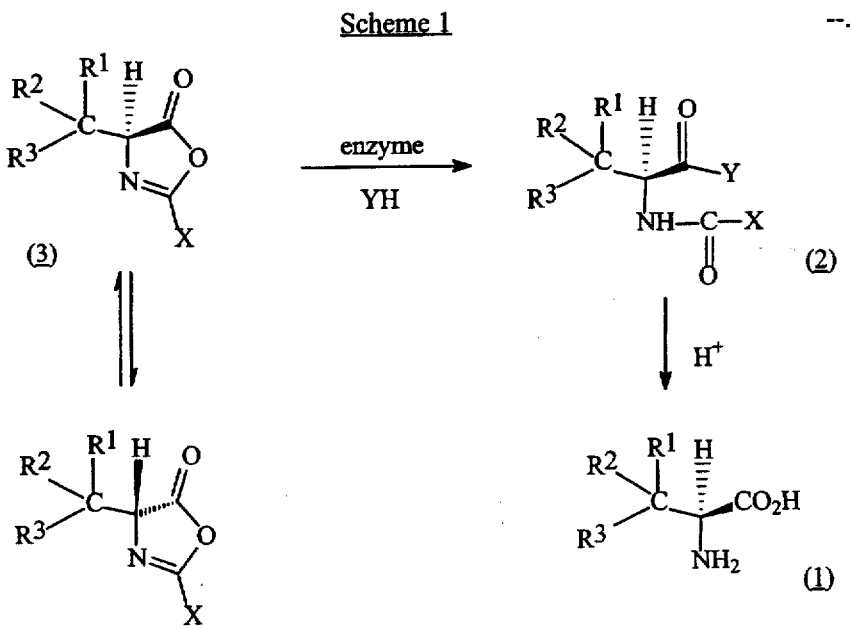

Scheme 1

UNITED STATES PATENT AND TRADEMARK OFFICE
CERTIFICATE OF CORRECTION

PATENT NO.    : 6,180,374 B1
DATED         : January 30, 2001
INVENTOR(S)   : Nicholas Turner, James Winterman, Raymond McCague It is certified that error appears in the above-identified patent and that said Letters Patent is hereby corrected as shown below:

Column 5,
Line 20,

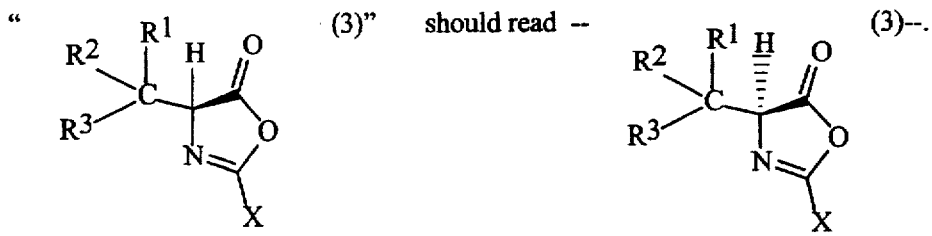

Column 6,
Line 9, "y=CH$_3$CH$_2$CH$_2$CH$_2$O" should read -- Y=CH$_3$CH$_2$CH$_2$CH$_2$O- --.

Signed and Sealed this

Fifth Day of February, 2002

Attest:

*Attesting Officer*

JAMES E. ROGAN
*Director of the United States Patent and Trademark Office*